United States Patent [19]

Vila et al.

[11] Patent Number: 5,089,472

[45] Date of Patent: Feb. 18, 1992

[54] USE OF GROWTH HORMONE RELEASING FACTOR FOR IMPROVING MENTAL FUNCTION

[75] Inventors: Francisco R. Vila; Thomás O. Alonso, both of Madrid; Ramón Cacabelos, La Coruña, all of Spain

[73] Assignee: Laboratorios Serono S.A., Switzerland

[21] Appl. No.: 206,100

[22] Filed: Jun. 13, 1988

Related U.S. Application Data

[63] Continuation-in-part of Ser. No. 148,667, Jan. 26, 1988, Pat. No. 4,939,124.

[51] Int. Cl.⁵ ............... A61K 37/02; A61K 37/24
[52] U.S. Cl. .................................. 514/12; 514/2; 514/21; 514/878; 514/879
[58] Field of Search ............... 514/2, 12, 878, 879, 514/21

[56] References Cited

U.S. PATENT DOCUMENTS 4,747,825   5/1988   Linkie ................................. 514/12
4,939,124   7/1990   Cacabelos ......................... 514/879

OTHER PUBLICATIONS

International Symposium on Somatostatin, Madrid, Spain, Oct. 7-8, 1986.
Cacabelos et al., *Hormone Research*, 29, 129-132 (1988).
Webster's Seventh New Collegiate Dictionary, G. C. Merriam Company, Springfield, Mass., 1967, p. 529.
Baudry in *Neutral Plasticity: A Lifespan Approach*, edited by Petit, Alan R. Liss, Inc., New York, 1988, pp. 125-141.
*International Symposium on Somatostatin*: Recent Advances in Basic Research and Clinical Applications held by The European Neuroendocrine Association, Madrid, Spain, oct. 7-8, 1986, Cacabelos et al.

*Primary Examiner*—F. T. Moezie
*Attorney, Agent, or Firm*—Ostrolenk, Faber, Gerb & Soffen

[57] ABSTRACT

Administration of a Growth Hormone Releasing factor (GRF) at effective dosage levels improves the mental function of attention or short term memory in a subject in need of the treatment. The method of treating comprises the administration to the subject of an effective mental function improving amount of a Growth Hormone Releasing Factor.

7 Claims, No Drawings

USE OF GROWTH HORMONE RELEASING FACTOR FOR IMPROVING MENTAL FUNCTION

This is a continuation-in-part of application Ser. No. 148,667, filed Jan. 26, 1988, and now U.S. Pat. No. 4,939,124, the disclosure of which is incorporated herein by reference.

This invention deals with a method for improving the mental function via the use of Growth Hormone Releasing Factor (GRF). Thus, pharmaceutical compositions containing GRF are administered by various routes to effect such improvement.

The somatotropinergic system (STS) is the only neuroendocrine axis in which specific stimulatory and inhibitory neuropeptidergic regulators have been demonstrated thus far. In normal conditions, growth hormone-releasing factor (GRF) and somatostatin (SS) are the hypothalamic hypophysiotropic hormones responsible for the regulation of growth hormone (GH) secretion.

At the same time, GRF and SS are influenced by central monoaminergic and peptidergic neuromodulators to optimize the functioning of the STS. See Cacabelos, R., Niigawa H., Hariguchi S. "Hypothalamohypophyseal system and brain function." J. Clin. Sci. 22:1108–1120 (1986).

Recent investigations suggest that the functional structure of the STS characteristically represented at the peripheral level might exist in the central nervous system (CNS). However, there is no exact knowledge on the way these two peptides exert their action at brain level.

In order to obtain more objective information about the changes that these peptides may induce in the activity of the CNS, studies were made to see if objective changes in the bioelectric activity of the brain were induced.

It has been discovered that GRF can effect improvement of the mental function in healthy individuals. More specifically, significant changes have been observed in such psychometric tests as short term memory and attention tests, as well as in EEG mapping.

Growth hormone releasing factor is the stimulatory growth-hormone releasing factor of the hypothalamus that assists in the neuroregulation of growth hormone secretion. It is compound No. 4416 in the *Merck Index*, 10th ed. (1983). Preferred for use herein are the segments or fragments designated as 1-44 and 1-29. Mixtures are operable. Pharmaceutical preparations used in accordance with the invention will contain GRF together with the optional inclusion of pharmaceutically acceptable vehicles. Peptide levels of approximately 1 to 10 mcg/kg body weight i.v. and of about 5 to approximately 50 mcg/kg body weight s.c. are operable.

The length of time for which the GRF-containing composition is administered can vary greatly. Useful times of administration depend upon the preferences of the treating physician.

Study Protocol and General Procedures 5 healthy volunteers of both sexes aged 18–25 years were admitted to this single blind study. Patients underwent the following procedures in a random way:
1. Baseline: registration of EEG (electroencephalogram), psychometric testing (short term memory), assessment of P-300 potential by audiometric testing.
2. The same after placebo (saline).
3. The same after GRF.

Each of phases 1 to 3 was followed by a period of at least one week before starting the next one.

Every patient underwent all 3 phases.

Dosage

GRF: 125 mcg i.v. (approx. 1.5–2.5 mcg/kg)
Saline: The same volume as used to dilute GRF.

Memory test (short term memory)

The memory test consisted in the memorization of a list of neutral words. The investigator read the words; then a dispersion phase ensued, consisting in the performance of some arithmetical tasks. The subject was then asked to repeat as many words from the list as he/she could remember.

The words used in each case were different, in order to avoid learning.

Attention Test

The aim of this test was to study the evoked potential P-300, known to be related with the attention span required to follow up and memorize a phenomenon.

The stimulus selected for this test was an auditive one, since audiometric testing of this potential has proven to be easy to perform and reliable. After a stimulus, a sound in this case, the mechanisms involved in the process of the hearing itself produce some bioelectric activity directly related to the stimulus itself. The perception process is more complex than the mere "hearing" and even after the stimulus has been removed, bioelectric activity related to it can be observed, as a form of 'echoes'. These 'echoes' are the evoked potentials. P-300 is a positive wave that can be observed 300 milliseconds after the first peak due to the stimulus, and it is known to be related with the conscious processing of it, namely with the attention devoted to it.

The subject hears some beeps of either 1000 or 2000 hertz, given in a random way. He is then asked to say how many high beeps (2000 hertz) were sent.

EEG Monitoring

EEG monitoring started 10 minutes after the injection and lasted through to the end of the tests (20–30 minutes).

Immediately after completing the first group of tests (i.e., 30–40 minutes after injection), the procedure recommenced with new words and beeps, under EEG monitoring.

Duration of the Session

Each session lasted about one hour from the injection.

EEG Mapping

This was performed with a PATHFINDER device.

A first screening of the maps for each frequency band (alpha, beta 1, beta 2, delta and theta) was performed, as well as for P-300.

Changes were defined as any variation in amplitude (potential) or in topographical distribution of the bands and were studied subject by subject, comparing the pattern obtained after injection of the products versus baseline recording and versus placebo.

The improvement in performance observed for the psychometric tests correlates with an impressive modification of the EEG patterns, both in amplitude and in the topographical distribution.

RESULTS

The analysis of the results focused on the most apparent changes in performance and/or EEG. After a preliminary Fourier's analysis, maps have been constructed for those frequency bands showing the most evident modifications, i.e., alpha, beta-2 and P-300.

Results of Psychometric Tests (memory)

The number of memorised words among the five subjects admitted to the study was the following (mean±sd):

Baseline : 8.4±1.34
Placebo : 12.4±3.13
GRF (10 min. after inj.) : 14.0±3.0
GRF (30–40 min. after inj.) : 16.2±2.38
Subject by subject, results appear as follows:

| Subject | Baseline | 30–40 min. after GRF |
|---|---|---|
| 1 | 9 | 15 |
| 2 | 7 | 16 |
| 3 | 10 | 19 |
| 4 | 7 | 18 |
| 5 | 9 | 13 |

Therefore, GRF enhances memorization capabilities. The importance of this observation is greatly increased by its correlation with the changes observed in the EEG maps, as shown below.

Analysis of Bioelectric Activity

Alpha waves

A net increase in energy was observed. Furthermore, in normal subjects at rest, the peak of alpha activity was mainly located at the right occipital lobe, near the midline of brain. Thirty to forty minutes after GRF, a clear spreading of the alpha activity over the whole brain was observed, suggesting an overall stimulation of brain activity, possibly related to non-specific stimulation of the activating reticular system.

Beta 2 waves

In normal circumstances, the main activity of beta 2 waves is mainly located at the left parieto-occipital area. The map after 30–40 min. from GRF administration, showed the following changes:

1. Overall spreading of beta 2 activity to the whole brain.
2. Increase in intensity at the initial left parieto-occipital focus (intensity more than doubled over the original values) and in extension of this focus.
3. Appearance of a new focus located at the right edge of the frontal lobe.

The left parieto-occipital lobe is known to be related to memory, so that an increase of electrical activity in this area correlates well with the findings in the performance test.

On the other hand, the appearance of a new focus of beta 2 activity at the frontal lobe (integration area) is interpreted as a consequence of the fact that the subjects construct certain logical associations in order to connect the neutral words to each other to form a sentence.

P-300 Activity

Again a net increase is observed in the P-300 energy 30–40 min. after administration of GRF. P-300 is an evoked potential known to be related to attention. This has been interpreted as the ability of the subject to 'devote a more intense attention to stimuli' after GRF than in baseline conditions.

Overall Interpetation

The effect of GRF is interpreted as an 'economizing' action, i.e., GRF favours the concentration of the 'available activity' in the areas where it is most needed.

We claim:

1. A method of improving the mental function of attention or short term memory in a subject in need of the treatment which comprises the administration to said subject of an effective mental function improving amount of a Growth Hormone Releasing Factor.
2. The method of claim 1 wherein the Growth Hormone Releasing Factor is administered at a dosage of about 1 to 10 mcg/kg intravenously.
3. The method of claim 1 wherein the Growth Hormone Releasing Factor is administered at about 5 to 50 mcg/kg subcutaneously.
4. The method of claim 1 wherein the Growth Hormone Releasing Factor is Growth Hormone Releasing Factor 1-44.
5. The method of claim 1 wherein the Growth Hormone Releasing Factor is Growth Hormone Releasing Factor 1-29.
6. The method of claim 1 wherein the mental function is memory.
7. The method of claim 1 wherein the mental function is attention.